United States Patent
Knapp

[11] Patent Number: 5,855,609
[45] Date of Patent: Jan. 5, 1999

[54] MEDICAL INFORMATION TRANSPONDER IMPLANT AND TRACKING SYSTEM

[75] Inventor: Terry R. Knapp, Neuchatel, Switzerland

[73] Assignee: Lipomatrix, Incorporated (BVI), Neuchatel, Switzerland

[21] Appl. No.: 375,811

[22] Filed: Jan. 20, 1995

Related U.S. Application Data

[63] Continuation-in-part of Ser. No. 938,833, Aug. 31, 1992, abandoned, and a continuation-in-part of Ser. No. 221,706, Apr. 1, 1994, Pat. No. 5,674,288, which is a continuation of Ser. No. 934,785, Aug. 24, 1992, Pat. No. 5,300,120.

[51] Int. Cl.$^6$ .................................. A61F 2/02; A61F 2/54
[52] U.S. Cl. .................................................. 623/11; 623/66
[58] Field of Search ................................. 623/7, 8, 11, 16, 623/66

[56] References Cited

U.S. PATENT DOCUMENTS

| | | |
|---|---|---|
| 3,839,708 | 10/1974 | Bredesen et al. . |
| 3,949,388 | 4/1976 | Fuller . |
| 4,262,632 | 4/1981 | Hanton et al. . |
| 4,361,153 | 11/1982 | Slocum et al. . |
| 4,399,821 | 8/1983 | Bowers . |
| 4,531,526 | 7/1985 | Genest . |
| 4,618,861 | 10/1986 | Gettens et al. ......................... 340/825.54 |
| 4,703,756 | 11/1987 | Gough et al. . |
| 4,730,188 | 3/1988 | Milheiser . |
| 4,746,830 | 5/1988 | Holland . |
| 4,854,328 | 8/1989 | Pollack . |
| 4,863,470 | 9/1989 | Carter . |
| 4,875,483 | 10/1989 | Vollmann ................................. 128/419 |
| 4,992,794 | 2/1991 | Brouwers . |
| 5,010,893 | 4/1991 | Sholder . |
| 5,012,286 | 4/1991 | Kawano et al. . |
| 5,028,918 | 7/1991 | Giles et al. . |
| 5,036,869 | 8/1991 | Inahara . |
| 5,041,826 | 8/1991 | Milheiser . |
| 5,084,699 | 1/1992 | DeMichele . |
| 5,095,309 | 3/1992 | Troyk et al. . |
| 5,211,129 | 5/1993 | Taylor et al. . |
| 5,218,343 | 6/1993 | Stobbe et al. . |
| 5,235,326 | 8/1993 | Beigel et al. . |
| 5,300,120 | 4/1994 | Knapp et al. . |

FOREIGN PATENT DOCUMENTS

| | | |
|---|---|---|
| 619 101 A1 | 10/1994 | European Pat. Off. . |
| WO8704900 | 8/1987 | WIPO . |
| WO9207505 | 5/1992 | WIPO . |

OTHER PUBLICATIONS trovan™ Electronic Identification Systems, Ltd. brochure for Model—ID 100, entitled "Implantable Transponder"; 4 pp.

Hughes Identification Devices brochure entitled "Injectable Transponder Small Size", 6 pp.

*Primary Examiner*—Debra S. Brittingham
*Attorney, Agent, or Firm*—Howell & Haferkamp, L.C.

[57] ABSTRACT

A passive electrical transponder may be encoded with a code corresponding to medical information, and the transponder directly transplanted in a patient's underarm area. Medical devices may also carry transponders to identify them for use with the system of the present invention. The code may be accessed with an electromagnetic hand held reader which is brought into proximity of the transponder. The medical information may itself be directly encoded into the transponder, or a code used which is then keyed to a corresponding data entry in a data bank or computerized data base accessible over telecommunication lines. With this invention, medical information may be reliably and confidentially recorded, maintained, and accessed with minimal patient involvement in order to achieve a high degree of reliability and accuracy. Also, medical information relating to patients and medical devices may be centrally collected over an extended time period and analyzed to generate recall notices, provide generalized health information and improve health care for all participants.

10 Claims, 2 Drawing Sheets

MEDICAL INFORMATION TRANSPONDER IMPLANT AND TRACKING SYSTEM

CROSS REFERENCE TO RELATED APPLICATIONS

This application is a continuation-in-part of Ser. No. 07/938,833, filed Aug. 31, 1992, now abandoned; and Ser. No. 08/221,706, filed Apr. 1, 1994, now U.S. Pat. No. 5,674,288, which is a continuation of Ser. No. 934,785, filed Aug. 24, 1992, now U.S. Pat. No. 5,300,120, the disclosures of all of the foregoing being incorporated herein by reference.

BACKGROUND AND SUMMARY OF THE INVENTION

Over the years, there have been many devices proposed for use in recording and associating medical information with an individual. Most commonly, this medical information includes the basic information necessary for emergency treatment such as blood type, allergic drug reactions, closest relative, any on-going medications, and other similar kinds of data. In the prior art, various kinds of fill-in-the-blank cards, tags, labels and the like are available for use. These may stored in a wallet, worn as a bracelet or necklace, associated with a shoe or other article of clothing, or otherwise associated or attached to an individual. These prior art devices have met with limited success, for various reasons.

One drawback encountered with these prior art devices is the limited amount of information which may be conveniently recorded and carried. Secondly, the information is typically recorded by the individual himself and is therefore subject to mistake and/or error due to the fact that the individual is rarely medically trained. Therefore, the medical information must first be obtained from a doctor or other trained medical personnel and errors may develop through merely communicating this information to the individual. For the same reason, not all of the more pertinent information may be recorded as it may not be known or appreciated by the individual. Similarly, updating the information occurs only haphazardly, subject to the whim of the individual. There may also be problems encountered in retrieving this information at the time of its need. The location of the data must first be ascertained, and then the data correctly read from the card or other means used to record the data. Unhappily, an individual's own handwriting may be sufficiently bad to prevent the reading of data even after location of the data card. Additionally, the data entry on the card may have been obliterated or otherwise obscured. All of these difficulties represent drawbacks in the various approaches in the prior art which have limited the widespread adoption and use of these prior art devices.

With the advance of technology, other problems and lost opportunities are increasingly experienced. The increasing sophistication of health care, in many cases relying on specialists who diagnose and treat patients upon referral from a general practitioner, develop information which is almost never routinely entered by an individual in any self kept medical data history. This specialized medical information is routinely available only in the specialist's files or records which is generally separated from that of the general practitioner. Information such as laboratory test results, specific diagnoses or prescriptions, and other related data thus becomes routinely unavailable except upon further inquiry from a knowing source. It is not believed that there is a standardized methodology for collecting all of this information in a single repository such as at the general practitioner's office.

This becomes increasingly important with the advent of science, proliferation of specialists, and increasing mobility of our civilized nations populations. Unless uncommon care is taken by an individual, his medical records are often remote from and even lost from use at the time of need. Not only is this important for routine examinations and consultations for medical problems, but increasingly so for emergency situations. This phenomenon diminishes the value of any self kept records including medical data information cards which, at most, is what emergency medical personnel may expect to find prior to administering any emergency medical treatment.

The inventors herein are also aware of a passive electrical transponder which has been used in the prior art to mark or identify inventory items and even livestock with an identifying number or code for inventory purposes. The passive electrical transponder is quite small, generally comprising a cylinder 2 mm in diameter by 11 mm in length, and its code may be conveniently read by an electromagnetic hand held reader. In operation, the hand held reader is brought into proximity of the transponder and emits a low frequency magnetic field to activate the passive transponder and thereby cause it to transmit its encoded data to the reader. With this particular commercial device, no battery or other source of electrical power is included in the passive transponder which helps contribute to its small size. One of the patents which have issued which describes these commercially available passive transponders and hand held readers is U.S. Pat. No. 5,041,826, the disclosure of which is incorporated by reference. In this patent, the patentee suggests that the primary object of the device is for identifying an object, animal or person. However, the inventors herein are not aware of any usage presently made of this device for identifying humans. Furthermore, this device is presently used to merely identify an object or the like for inventory purposes, and such application would not seem to be particularly adaptable for use with humans as much less intrusive and convenient means are already available for such purposes, including driver's licenses, and other forms of "identification".

The inventors herein are also the inventors of the combination of a passive transponder and surgically implantable implants as disclosed and claimed in one of the parent applications and patent mentioned above. This good and valuable invention provides a ready means for identifying a particular prosthesis, including details relating to its manufacturer, date of manufacture, model number, and other desired data. This invention provides a ready means for complying with the Safe Medical Devices Act of 1990 and its reporting and record keeping requirements. This information and tracking is generally performed by a medical practitioner, in many cases the same practitioner who surgically implanted the prosthesis, and the data relating thereto maintained in the medical practitioners files. There is no system or methodology for reporting and recording this data, and updating it, in a centralized data bank which could be extremely useful for statistical analysis to track failure rates or otherwise form the basis for recommended action with respect to the existing user population. Additionally, the Safe Medical Devices Act of 1990 mandates reporting and record keeping requirements for medical devices beyond those which are surgically implanted. Examples of these include infusion pumps. Currently, there are over 250 makes and models of mechanical infusion pumps to deliver nutrition, drugs, hormones, and fluids to patients. Morphine pumps are used to deliver chronic pain relief. Food infusion pumps deliver nutrients to post operative patients as well as the premature, disabled, and elderly. Drug infusion pumps are used for treatment of a wide variety of clinical disorders including Aids, hemophilia, and diabetes. Should the infusion device leak, under or over infuse, or otherwise malfunction, the patient can suffer dire consequences and even die. Ventilators are another example of devices common in hospitals, hospices, nursing homes, and home health care applications. Again, if the ventilator should malfunction, the patient could suffer dire consequences. Various kinds of monitors including pulse oximeters and apnea ($CO_2$) monitors are devices used very commonly in hospitals and even in home care situations to monitor critical respiratory parameters. If these devices fail to properly monitor and appropriately warn, a patient could suffer dire consequences. The Tokos systems to prevent premature birth are another example of a monitoring system used in home health care. All of these various devices are subject to FDA adverse event reporting, warning notices, manufacturer recalls, etc. Identification and tracking of these devices and their use with patients has become mandatory as a result of the Safe Medical Devices Act of 1990.

The reporting requirements mandated require the owner of these various devices to keep detailed records of every patient who has ever used a particular piece of equipment. Accordingly, if an infusion pump is used in a hospital setting by 100 different patients over its useful life, the hospital must maintain these records. Proper sterilization, maintenance, and re-calibration testing records must also be scrupulously maintained. These reporting and tracking requirements represent a significant burden of administrative effort not presently funded or staffed by hospitals and will impact the cost of health care.

In a novel and unique approach, the inventors herein have succeeded in conceiving of the use of the passive transponder for direct implantation in a human with the transponder being encoded to correspond to appropriate medical information in one of several ways. In practice, the passive transponder would be encoded and would then be implanted directly into a human in a conveniently accessible location, such as under the arm in the armpit. Because of its small size, it would be unobtrusive and barely even noticeable to the patient. At the same time, the transponder could be encoded in one of several ways to provide ready and complete access to a wide variety of medical information. Furthermore, the medical information will have been verified and stored by trained medical professionals such that its accuracy can be relied upon even in emergency situations.

With presently commercially available devices, the transponder may be encoded with up to sixty-four binary bits of data. This memory size is expected to be increased as the passive transponder is further developed and improved over time. With this memory size, much information could be directly encoded and stored in the transponder itself. With at least one commercial device, there are three different ways to encode information into the transponder. The first of these is to encode the information at the time that the chip is manufactured. Ordinarily, if encoding is performed at this time, then a unique number would be encoded into the transponder and it could then be used to access data stored in a data bank, as explained more completely herein. Secondly, the memory chip may be encoded after manufacture, but prior to sealing the chip into the transponder envelope. If the chip were to be encoded at this stage, then custom encoding could be achieved which could be medical information associated with any particular patient. Thirdly, the chip could be manufactured and sealed in the transponder envelope without encoding, and perhaps even implanted in the patient. Encoding could then take place through a read/write operation with the electromagnetic reader as described herein. If encoded in this manner, custom encoding could be utilized to directly encode the transponder with medical information corresponding to the particular patient. With any of the three methods for encoding the transponder, a unique identifier may be utilized and the identifier used to access data in a remote data bank.

The encoded information contained in the passive transponder could be used to access a data bank which would be immediately available, for example over telephone lines, such that trained medical personnel could readily obtain the medical information on an emergency basis. With the remote data bank option, the amount of data which may be stored is virtually unlimited, the data bank may be updated or changed as the patient's information changed, and all of this data entry, alteration, and accessing would be handled by trained personnel in order to provide reliable medical data for the safety and benefit of the patient, as well as for reduced legal liability.

In addition to medical data relating to individual patients, data relating to medical devices and their use with patients may also be readily recorded and tracked using the transponder methodology. As noted in the parent application and patent mentioned above, transponders may be associated with surgically implantable prostheses. Data relating to these implants may be regularly collected and transmitted to a central data base which can record and track the data. Statistical analyses may be readily performed on the data at the data base in a secure manner through various methodologies and the results provided to various interested individuals and organizations with access limited by an audit or oversight commission. Furthermore, the transponder methodology may also be extended to non-implanted medical devices such as the infusion pumps, ventilators, and monitors mentioned above. Indeed, for purposes of the present invention, a medical "device" may be presumed to include any sort or manner of object, thing, or other assemblage which is related to health care. Other examples include transplanted tissue such as organs, skin, etc., heart valves, pace makers, and any other medical device, appliance, or thing which would provide usefulness to a patient over an extended period of time such as several years. Further examples include implants comprised of other mammalian tissue, cells, or composite devices such as genically engineered cells incorporated directly into an implantable device. Cornea transplants and blood vessel grafts are still further examples.

The wealth of medical data which is presently available, and its increasing amount and complexity, is creating a strain on the present medical data collection and recording systems which creates a long felt need for the present invention. One of the sad experiences of the world is the proliferation of the Aids virus for many years without detection due in large part to the lack of a centralized medical information data base through which statistical analysis could have identified this disturbing epidemic at a stage much earlier than that experienced. Societal concerns as to confidentiality can be satisfied through a "blue ribbon" international audit and oversight commission which could control access to the data base as well as the various statistical analyses which could prove highly beneficial for tracking various kinds of medical devices as well as the health condition of the many individuals who participate in the data base system of the present invention. There are many encoding schemes which are presently available so as to limit the access of any third party user who desires to access an individuals data for treatment or who wishes to update medical data for any particular patient after an examination, laboratory tests, or the like. For example, the data base could be segmented and separate look up tables provided to match particular patient i.d.'s with their individual data base entries. Any statistical analysis or other processing of the data base information could be performed without any access to the individual patient i.d. or look up table information to thereby preserve confidentiality and yet generate highly valuable statistical information relating to any data recorded in the data base. This applies both to patient information as well as medical device information. For third party users, access to the data base can be very "user friendly" such as by telecommunication over any telephone using a modem as is well known in the art. A computer or other input/output device could be used, with the proper i.d. information both to gain access to the data base as well as any individual patient records kept in the data base. Depending upon the desires of the patients, access may be as restricted or open as he desires, within limits. Furthermore, provision may be made for changing the accessibility of patient data over the life of the patient.

As is well known, there may be tremendous legal liability which could result from reliance on inaccurate data. This inaccurate data could result in any one of the many ways discussed above in connection with the prior art attempts to solve this problem. With the present invention the legal liability would be effectively minimized and could also be isolated and controlled for insurance purposes with those who are trained and skilled in handling this kind of data. With these advantages, it is expected that many medical personnel will welcome the adoption and implementation of the present invention.

While the principal advantages and features of the present invention have been described above, a more complete and thorough understanding of the invention may be attained by referring to the drawing and description of the preferred embodiment which follow.

DETAILED DESCRIPTION OF THE PREFERRED EMBODIMENT

Figure 1:
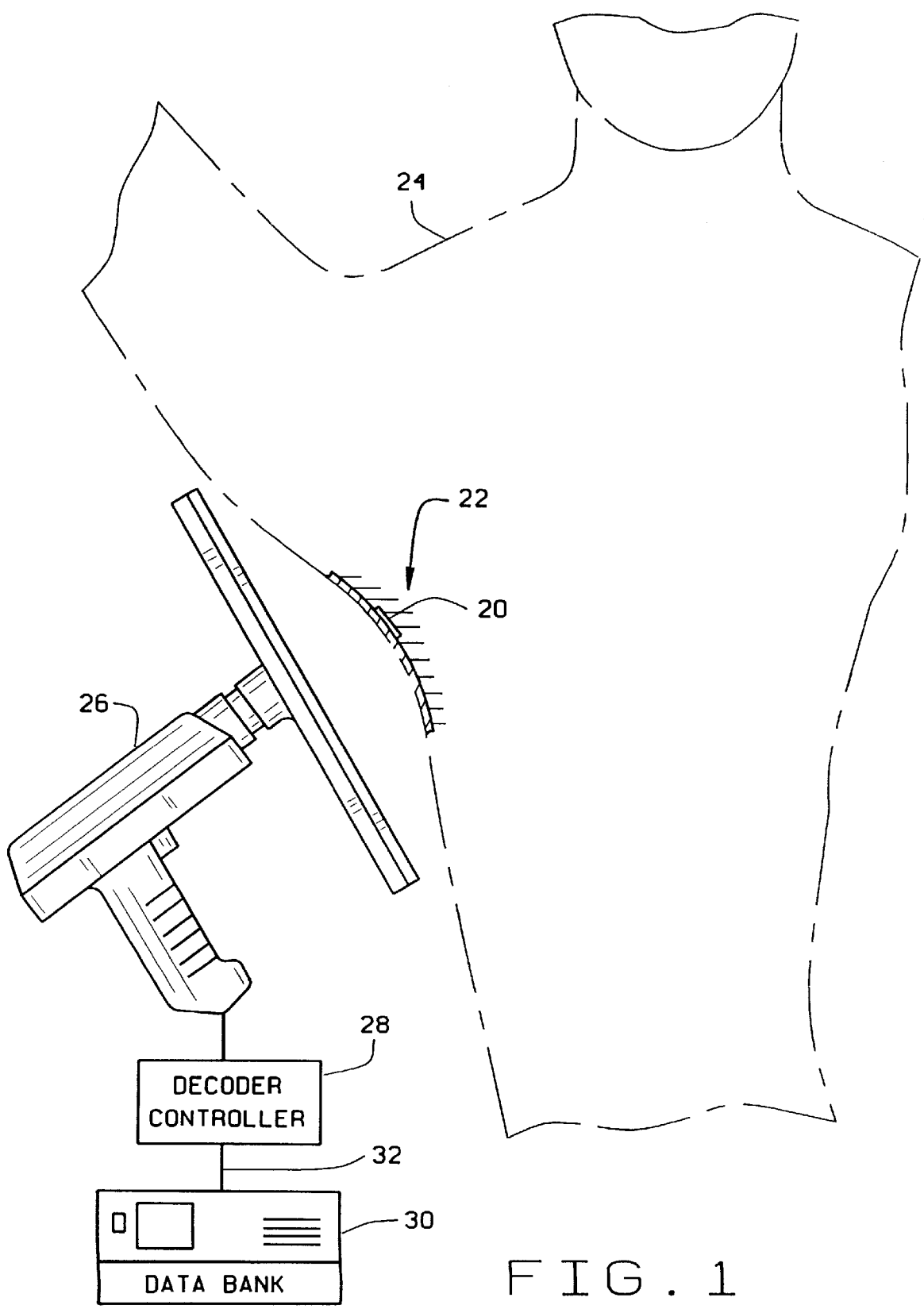
FIG. 1 is a perspective view of a passive transponder implanted in the underarm of a patient with a non-invasive reader disposed for reading its encoded data, the reader being connected to a decoder/controller which in turn is connected to a data bank.

As shown in FIG. 1 of the drawings, a passive transponder 20 may be conveniently implanted just beneath the skin and the underarm area 22 of a patient 24. A hand held electromagnetic reader 26 may be brought into close proximity of the passive transponder 20 and its encoded information read thereby in a non-invasive manner. Similarly, the electromagnetic reader 26 may be used in a read/write mode to directly encode the transponder 20. Alternately, the memory chip (not shown because of its relatively smaller size) contained in the transponder 20 may be encoded at the time of manufacture or prior to its being sealed in the transponder 20. A decoder controller 28 may be used to display the encoded information and also, decoder controller 28 may be used to access a data bank 30 over a telecommunication line 32, such as a telephone connection or the like.

With presently available commercial devices, the passive transponder 20 may be encoded with up to sixty-four binary bits of data for the direct encoding and reading therefrom of medical information including blood type, allergic reactions, on-going medication, and such other information as might be needed or desirable. In a second mode of implementation, the encoded information contained within the passive transponder 20 may instead be used to access data bank 30 over telecommunication lines 32 in order to obtain the same, or even a much larger amount of information relating to the particular patient 24. With this second mode of implementation, the data entries contained in data bank 30 may be conveniently altered, updated, or otherwise modified by trained medical personnel to maintain the information current with respect to the particular patient 24 as time passes. The accuracy and reliability of the data, whether encoded directly in passive transponder 20 or stored in data bank 30, is expected to be virtually flawless in view of the fact that only trained personnel will be entering data as opposed to relying on individual patients determining and entering their own data on personal ID cards or other prior art devices as are presently in use.

Figure 2:
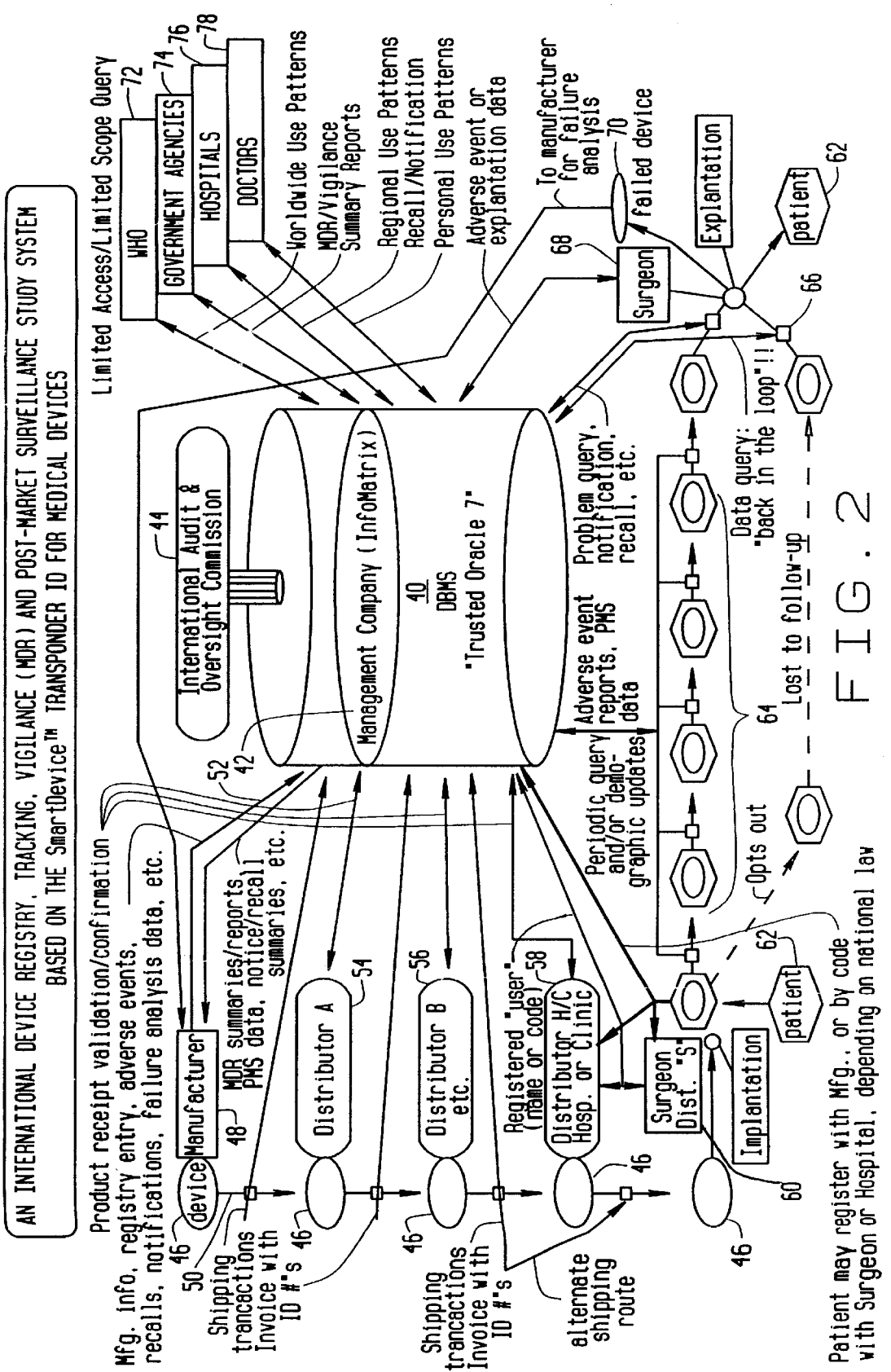
FIG. 2 is a schematic diagram illustrating the flow of data between users of the computerized data base at various times over a patient and/or medical device lifetime.

As shown in FIG. 2, the data bank 30 may be a computerized data base 40 operated by a computer 42 controlled and run by a management company on an ongoing basis. An international audit and oversight commission 44 has ultimate supervisory and oversight control of the operation of the computerized data base 40. An operational time line is depicted and shown generally peripherally about the computerized data base 40 in FIG. 2 to illustrate the flow of data to and from the computerized database 40 over an extended time period, such as several years extending to several decades over the life of a patient or medical device. In order to illustrate many of the capabilities of the computerized data base 40 and system of the present invention, the data relating to a medical device interacting with a patient is also illustrated and will now be explained.

A medical device 46 is initially manufactured by a manufacturer 48 and a transponder 50 may be associated with device 46 to identify the device 46 and, optionally, store other information in addition to identifying data. At the same time, manufacturing information, registry entry, adverse events, recalls, notifications, failure analysis data, etc. may be telecommunicated through a data link 52 to the computerized data base 40 by manufacturer 48. Upon initial manufacture, it is anticipated that minimal data will be entered in order to identify the device. However, other additional data such as manufacturing lot, serial number, model number, etc. may also be entered and stored in transponder 50. Other kinds of data may be provided by the computerized data base 40 to the manufacturer 48 such as summaries, reports, PMS data, notice/recall summaries, or other data which would be important or of interest to a manufacturer may be provided either periodically, on an as needed basis, or upon inquiry from a manufacturer 48. When device 46 is sold or transported through the distribution chain, such as through Distributor A 54 and Distributor B 56, various shipping information is provided to the computerized data base 40 and product receipt validation/confirmation information may be exchanged between each Distributor 54, 56 and data base 40. Eventually, device 46 will wind up in the hands of a hospital or clinic 58, or a surgeon 60 when the device will be, for example, implanted to a patient 62. At that time, additional exchange of data takes place with computerized data base 40 so as to indicate to the computerized data base that a patient 62 has been associated with a medical device 46. For purposes of illustration as shown in FIG. 2, this is illustrated as an implantation of a prosthesis. As has been explained above, other kinds of associations may take place between medical devices 46 and patients 62 which do not require implantation and which are presently required to be reported and tracked in compliance with federal law. Association or use of medical devices 46 on patients 62 may also be tracked and recorded by communicating with computerized data base 40.

As the patient interacts with medical device 46, periodic examinations may take place which represent times at which data may be updated in computerized data base 40. Such examinations may detect problems with medical device 46, failures, malfunctions, or other adverse events may be reported. At any point in this life cycle 64, a patient may "opt out" and be lost to follow up until some time in the future at which time a physician or other health care giver is consulted as illustrated at point 66. At that time, communication may be made with the computerized data base 40 and interaction may take place with a surgeon 68 who may or may not be the same surgeon 60 who implanted the original medical device 46. Such identity of surgeons is not required as any surgeon 68 may access that particular patient's medical information stored in computerized data base 40 and obtain a complete history of the patient's association with medical device 46 and his reported experiences. In some instances, there may be no reported check-ups, examinations, or other information. At the other extreme, continuous data may be available and recorded giving a complete history of the patient's experience with the particular medical device 46 over what may be many years. As an illustration of the power of the computerized data base 40, upon consultation with surgeon 68, the surgeon may be advised that statistical analyses or other analysis of data in the computerized data base 40 has demonstrated a need to remove or explant a failed device 70, or a device subject to unacceptable future risk, from patient 62. In that instance, the device 70 may be readily provided back to its original manufacturer for failure or other analysis using information obtainable from computerized data base 40.

While the computerized data base 40 and system of the present invention provides many advantages to individual patients and specific manufacturers of medical devices, it also provides a wealth of information which may be effectively used in a confidential manner by health organizations, government agencies, hospitals, and even doctors as an aid in improving the quality of health care. Examples of these are illustrated in FIG. 2 wherein an international organization, such as the World Health Organization 72 may interact with the data base 40 to learn worldwide use patterns of medical devices 46 and other world health issues relating to diseases, treatments, etc. Governmental agencies 74 may interact with the data base 40 to directly collect the medical device registry data including summary reports in compliance with federal laws and regulations. Upon extension of the present invention internationally, compliance with international treaties and other governmental requirements may also be satisfied. Hospital 76 may interact with the data base 40 to determine regional use patterns, recall/notification of medical device 46 failure or malfunction, or for other reasons such as regional health care issues for a particular patient populations and the like. Doctors 78 may also be provided access to data base 40 to help determine, within the context of a Doctor's own practice, the effectiveness of various protocols, procedures, and treatments for particular patients with particular diagnoses.

There are various changes and modifications which may be made to the invention as would be apparent to those skilled in the art. However, these changes or modifications are included in the teaching of the disclosure, and it is intended that the invention be limited only by the scope of the claims appended hereto.

What is claimed is:

1. A system for recording and tracking medical information relating to a plurality of individuals over an extended time period, said system comprising:

an implantable transponder for each of the individuals, said transponder being adapted to communicate a unique identification code to a reader, at least some of said transponders being associated with a medical device;

a reader adapted to communication with said transponder; and a remote data base separate from said transponder and external to the individuals and adapted to store and retrieve medical information in correspondence with a plurality of identification codes including said unique identification code; a decoder controller adapted to communicate with said reader, to communicate said unique identification code to said data base, and to communicate at least a portion of said medical information to and from said data base;

said medical information stored in said remote data base including data relating to said associated medical devices so that said medical device data can be conveniently updated over time and made available for use by qualified medical practitioners.

2. The system of claim 1 further comprising means for analyzing data stored in said remote data base to determine operational parameters relating to any of said medical devices.

3. The system of claim 2 wherein said operational parameters include a failure rate.

4. The system of claim 1 wherein said medical devices include surgically implanted prostheses.

5. The system of claim 4 further comprising means for analyzing data stored in said remote data base to determine operational parameters relating to any of said medical devices.

6. The system of claim 5 wherein said operational parameters include a failure rate.

7. A medical information system for recording and tracking medical information relating to a plurality of individuals over a number of years, said data base and system comprising:

a centralized, computer controlled data base containing medical information relating to the plurality of individuals;

a plurality of input/output devices, said data base being accessible through said plurality of input/output devices for accessing and updating said medical information;

means associated with each individual for identifying the individual and the individual's related medical information recorded in said data base, said association means being adapted for surgical implantation in its associated individual to thereby be permanently available for use by any medical practitioner; and a medical device associated with at least one of the individuals wherein said at least one individual's medical information includes data relating to said medical device, said medical device also being associated with said associating means.

8. The medical information system of claim 7 wherein said medical device is adapted for surgical implantation.

9. A method for recording and tracking medical information relating to a plurality of individuals over an extended time period, said method comprising the steps of:

associating transponders with the individuals by implanting one of the transponders in each of said individuals, wherein each of said implanted transponders is adapted to communicate a unique identification code, at least some of said transponders being associated with a medical device;

collecting medical data during consultation of one of the associated individuals during consultation with a medical practitioner including collecting medical data relating to said medical devices;

communicating with the consulted individual's transponder to receive the consulted individual's transponder's unique identification code;

communicating the consulted individual's transponder's unique identification code to a remote, centralized data base separate from the individual's transponder and external to the individual; and updating a data file associated with the individual's transponder's unique identification code in said data base with said collected medical data so that information relating to said medical devices is collected and maintained in said centralized data base.

10. The method of claim 9 further comprising the step of analyzing data stored in said centralized data base to determine operational parameters relating to any of said medical devices.

* * * * *